(12) United States Patent
Fukuzawa

(10) Patent No.: US 8,480,969 B2
(45) Date of Patent: Jul. 9, 2013

(54) MEDICAL DEVICE AND COVER STRUCTURE

(75) Inventor: Masahiro Fukuzawa, Kyoto (JP)

(73) Assignee: Arkray, Inc. (JP)

( * ) Notice: Subject to any disclaimer, the term of this patent is extended or adjusted under 35 U.S.C. 154(b) by 263 days.

(21) Appl. No.: 12/896,431

(22) Filed: Oct. 1, 2010

(65) Prior Publication Data

US 2011/0021884 A1    Jan. 27, 2011

Related U.S. Application Data

(63) Continuation of application No. PCT/JP2009/000928, filed on Mar. 2, 2009.

(30) Foreign Application Priority Data

Apr. 7, 2008   (JP) .................................. 2008-099192

(51) Int. Cl.
*G01N 21/75*   (2006.01)
*B65D 85/38*   (2006.01)

(52) U.S. Cl.
USPC ............ 422/401; 206/1.5; 206/305; 206/438

(58) Field of Classification Search
USPC ................. 206/1.5, 305, 307, 320, 438, 449, 206/455, 468; 220/345.1–345.4, 348; 422/68.1, 422/50, 400, 401; 436/46, 50, 55; 600/309, 600/318, 322, 368, 583
See application file for complete search history.

(56) References Cited

U.S. PATENT DOCUMENTS

| 4,126,224 | A | * | 11/1978 | Laauwe et al. | 206/1.5 |
|---|---|---|---|---|---|
| 4,366,915 | A | * | 1/1983 | Seidler | 206/1.5 |
| 4,807,759 | A | * | 2/1989 | Castner | 206/1.5 |
| D393,313 | S | | 4/1998 | Meisner et al. | |
| D444,235 | S | | 6/2001 | Roberts et al. | |
| D484,600 | S | | 12/2003 | Kaar et al. | |
| D495,418 | S | | 8/2004 | Rounds et al. | |
| D537,164 | S | | 2/2007 | Shigemori et al. | |
| D545,438 | S | | 6/2007 | Huang et al. | |
| D546,216 | S | | 7/2007 | Bolognesi et al. | |

(Continued)

FOREIGN PATENT DOCUMENTS

| JP | 03-206942 | 9/1991 |
|---|---|---|
| JP | 04-020272 | 2/1992 |

(Continued)

OTHER PUBLICATIONS

International Search Report; PCT/JP2009/000928; Apr. 14, 2009.

(Continued)

*Primary Examiner* — Luan K Bui
(74) *Attorney, Agent, or Firm* — Studebaker & Brackett PC

(57) ABSTRACT

A medical device includes a casing, a cover member that covers a portion on one-direction side of the same, and a sheet member interposed therebetween. The cover member includes on its periphery a hook part having a hook-like portion and a protrusion. The casing includes a latch part configured to engage with the hook part and a fitted portion for the protrusion to fit in. The sheet member includes an alignment part for aligning itself with the cover member. The cover member preferably has optical transparency. The casing preferably includes a recess shaped to fit with an outer shape of the cover member at a portion to be covered by the cover member.

10 Claims, 11 Drawing Sheets

U.S. PATENT DOCUMENTS

| | | | |
|---|---|---|---|
| D546,454 S | 7/2007 | Gutmann et al. | |
| D546,457 S | 7/2007 | Hannant et al. | |
| D546,458 S | 7/2007 | Hannant | |
| D549,830 S | 8/2007 | Behar et al. | |
| D550,364 S | 9/2007 | Glover et al. | |
| D551,350 S | 9/2007 | Lorimer et al. | |
| 7,275,642 B2 * | 10/2007 | Yuhara | 206/1.5 |
| D567,125 S | 4/2008 | Okabe et al. | |
| 2004/0226856 A1 * | 11/2004 | Yuhara | 206/581 |
| 2005/0155886 A1 * | 7/2005 | Nakajo | 206/455 |

FOREIGN PATENT DOCUMENTS

| | | |
|---|---|---|
| JP | 2003-107092 A | 4/2003 |
| JP | 2003-198158 A | 7/2003 |
| JP | 2003-345092 A | 12/2003 |
| JP | 2004-313269 A | 11/2004 |
| JP | 2005-202223 A | 7/2005 |
| JP | 3127674 | 11/2006 |
| JP | 2007-50231 A | 3/2007 |
| JP | 2008-042824 A | 2/2008 |
| JP | 2008-048071 A | 2/2008 |
| WO | 2009/075065 A1 | 6/2009 |
| WO | 2009/075066 A1 | 6/2009 |

OTHER PUBLICATIONS

Japanese Office Action "Notification of Reasons for Refusal" dated May 16, 2012; Japanese Patent Application No. 2010-507131 with translation.

* cited by examiner

MEDICAL DEVICE AND COVER STRUCTURE

CROSS-REFERENCE TO RELATED APPLICATIONS

The present application is a continuation of International Application No. PCT/JP2009/000928, filed Mar. 2, 2009, which claims priority to Japanese Patent Application No. JP2008-099192, filed Apr. 7, 2008, the entire contents of each of these applications being incorporated herein by reference in their entirety.

BACKGROUND OF THE INVENTION

1. Field of the Invention

The present invention relates to medical devices, and particularly to a portable medical device.

2. Description of the Background Art

Recently, the size reduction of medical devices has advanced, and the sizes of medical devices such as glucose meters, sphygmomanometers, and pulse rate meters, for example, have been reduced to such a degree that they are portable. Such medical devices are often carried around by patients, medical personnel, and the like, and their frequency of use is high. In particular, the glucose meter is an indispensable medical device for diabetic patients to always carry with them, and thus is a highly personal medical device.

Users of such highly personal devices have a desire to customize the appearance of the devices according to their preferences, thereby expressing their individuality. In response to such a desire, covers that enable the users to customize the appearance of medical devices according to their preference have been proposed recently (for example, see Japanese Patent Application Publication No. 2003-107092 (hereinafter referred to as Patent document 1) and Japanese Patent Application Publication No. 2004-313269 (hereinafter referred to as Patent document 2)).

More specifically, Patent documents 1 and 2 disclose a cover on a surface of which a pattern or a design is printed. The user can customize the appearance of the device by using a cover provided with a design of his or her preference. As a result, the user is prevented from losing interest in that particular device model, which encourages the user to use the same device model for a long time. Furthermore, this promotes the extension in life cycle of the device, thereby reducing the environmental load.

Customizing the appearance with a cover is frequently employed in a field of portable phones. Japanese Registered Utility Model Publication No. 3127674 (hereinafter referred to as Patent document 3), for example, discloses a cover to be attached to a casing of a portable phone. The cover is transparent on which neither a pattern nor a design is printed, but a sheet exhibiting a pattern, a design, or a photograph is inserted between the casing of the portable phone and the cover. Thus, changing only the sheet realizes easy alteration in the appearance and easily increases variations in customizations. The cover of Patent document 3 seems to be applicable also to medical devices.

The covers disclosed in the above Patent documents 1 and 2 need to cover not only the front surface but also the side surfaces of a medical device, and thus are structurally voluminous. Therefore, attaching the covers disclosed in the Patent documents 1 and 2 to a medical device causes a problem of obstructing size reduction of the devices.

Moreover, altering the appearance by the covers disclosed in Patent documents 1 and 2 requires replacement of the covers per se. Thus if a user desires to enjoy various appearances, multiple covers with different designs are needed. Then the above-described voluminous structure causes a problem of a lot of storage space.

In contrast, since the cover disclosed in Patent document 3 does not have to cover the side surfaces of a device, and thus is not voluminous, adopting this cover to a medical device appears to prevent obstruction of size reduction of the device. The problem of storage space for a user also appears to be solved.

However, the cover disclosed in Patent document 3 requires attachment to the casing by screw. It further requires arrangement of the sheet in a predetermined position beforehand, before screwing. Thus, with the cover disclosed in Patent document 3, complicated work with a tool is required every time a user attaches and detaches the cover. Employing a screw tightened easily by hand appears to reduce complicatedness of work. In such a case, however, the head of the screw needs to be large, which obstructs size reduction of the device, in the same way as in Patent documents 1 and 2.

SUMMARY OF THE INVENTION

It is an object of the present invention to provide a cover structure and a medical device using the same that solves the above-described problem, and facilitates attachment and detachment of a cover, while preventing obstruction of size reduction of a device.

In order to achieve the above-described object, a medical device according to the present invention is a medical device that measures a condition of a living body, including a casing, a cover member that covers a portion on one-direction side of the casing, and a sheet member interposed therebetween, the cover member including on its periphery a hook part having a hook-like portion and a protrusion, the casing including a latch part configured to engage with the hook part and a fitted portion for the protrusion to fit in, and the sheet member including an alignment part for aligning itself with the cover member.

With the medical device according to the above present invention, the cover member is not voluminous, unlike conventional covers that cover the front surface and the side surfaces of a casing at a time. Thus the medical device according to the present invention prevents obstruction of size reduction of a device. Furthermore, even if a user owns many cover members, the user do not need a lot of storage space, and thus storage is easy. Moreover, since the cover member is attached by engaging the hook part with the latch part and then fitting the protrusion in the fitted portion, in the medical device according to the present invention, attachment and detachment of the cover member is facilitated.

In a preferred mode of the above-described medical device of the present invention, the casing includes a recess shaped to fit with an outer shape of the cover member at a portion to be covered by the cover member, the latch part is provided in a position of a side wall of the recess corresponding to the hook part, and the fitted portion is provided in a position of the side wall corresponding to the protrusion. In this mode, since the cover member is housed in a space inside the recess provided in the casing, obstruction of size reduction of a device is further prevented.

In the above mode, it is preferable that in the medical device according to the above present invention, the hook part is shaped such that a tip of the hook-like portion faces an opposite side from a casing side when the cover member is arranged on the casing, and the recess is configured to allow the hook part to move to a bottom surface side of the recess when the hook part of the cover member is pushed. In this case, pushing the cover member from outside easily disengages the hook part from the latch part. Thus detachment of the cover member is further facilitated.

Also in the above mode, it is preferable that the cover member is in the form of a plate and includes two opposing side surfaces, each of the side surfaces having the protrusion, the hook part is arranged on a virtual axis being parallel to the two side surfaces and passing between the protrusions, and the side wall of the recess is shaped such that a portion located on the virtual axis when the cover member is attached and opposing a position corresponding to the hook part is lower than another portion. In this case, the cover member is detached only by disconnecting the hook part from the latch part and then sliding the cover member in a direction away from the latch part along the above-described virtual axis.

Also in the above mode, it is preferable that in the medical device according to the above present invention, the latch part includes a hole arranged in a position of the side wall of the recess corresponding to the hook part and a projection provided inside the hole, the hole is provided so as to allow insertion of the hook-like portion, and the projection is configured to engage with the hook-like portion. In this case, since the latch part is contained inside the side wall, a gap between the cover member and the casing is reduced in size, and thus unity between the both is produced when observed from outside.

Further in the above mode, it is also preferable that in the medical device according to the above present invention, the latch part includes a hole arranged in a position of the side wall of the recess corresponding to the hook part and a pair of projections provided inside the hole, the hole is provided so as to allow insertion of the hook-like portion, and the pair of projections are configured such that the hook-like portion is located between the pair of projections and either one or both of the projections engage with the hook-like portion.

Moreover, in the above mode, it is also preferable that in the medical device according to the above present invention, the fitted portion include a first groove and a second groove in a position of the side wall corresponding to the protrusion, the first groove is provided from an opening of the recess along the depth of the recess, and the second groove is provided so as to intersect with the first groove. In this case, the protrusion of the cover member is fitted into the fitted portion only by superposing the cover member over the opening of the recess and then sliding the cover member. In the case of releasing from the fit, only sliding the cover member is sufficient.

In the medical device according to the above present invention, the alignment part of the sheet member is preferably configured to engage with a part of the cover member. In this case, alignment of the sheet member is facilitated.

Moreover, in the medical device according to the above present invention, the cover member preferably has optical transparency. In this case, changing only the sheet member realizes alteration in the appearance, and necessity for the user to have many cover members is reduced. Further in this case, preferably the medical device according to the above present invention further includes a display screen that displays a measurement result, the display screen being arranged at a bottom surface of the recess, and the sheet member including an open part that exposes the display screen. In the above mode, the cover member protects the display screen, and durability of the medical device is increased.

Moreover, in order to achieve the above-described object, a cover structure according to the present invention includes a base, a cover member that covers a portion on one-direction side of the base, and a sheet member interposed therebetween, the cover member including on its periphery a hook part having a hook-like portion and a protrusion, the base including a latch part configured to engage with the hook part and a fitted portion for the protrusion to fit in, and the sheet member including an alignment part for aligning itself with the cover member.

The cover structure according to the present invention is applicable to medical devices, and further to devices such as portable phones, PDAs, and electronic dictionaries, and in such a case, the same advantages as the above-described advantages of the medical device according to the present invention can be obtained. Moreover, the same modes as the above-described preferable modes of the medical device according to the present invention can be employed also for the cover structure according to the present invention.

As stated above, a cover structure and a medical device according to the present invention facilitate attachment and detachment of a cover, while preventing obstruction of size reduction of a device.

These and other objects, features, aspects and advantages of the present invention will become more apparent from the following detailed description of the present invention when taken in conjunction with the accompanying drawings.

BRIEF DESCRIPTION OF THE DRAWINGS

FIG. 3A is an enlarged perspective view illustrating an enlarged part of the cover member illustrated in FIG. 1. FIG. 3B is an enlarged perspective view illustrating an enlarged part of the sheet member illustrated in FIG. 1, and FIG. 3C is an enlarged perspective view illustrating an enlarged part of another example of a sheet member.

FIGS. 5A to 5C illustrate a series of attachment steps and FIG. 5D illustrates a detachment step.

FIG. 7A is an enlarged perspective view illustrating the enlarged hook part, and FIG. 7B is an enlarged perspective view illustrating the enlarged alignment part.

FIG. 8A is an enlarged perspective view illustrating the enlarged hook part, and FIG. 8B is an enlarged perspective view illustrating the enlarged alignment part.

FIG. 9A is an enlarged perspective view illustrating the enlarged hook part, FIG. 9B is an enlarged side view illustrating the enlarged side surface of the hook part, and FIG. 9C is an enlarged perspective view illustrating the enlarged alignment part.

FIG. 10A is an enlarged perspective view illustrating the enlarged hook part, FIG. 10B is an enlarged side view illustrating the enlarged side surface of the hook part, and FIG. 10C is an enlarged perspective view illustrating the enlarged alignment part.

FIG. 11A is an enlarged perspective view illustrating the enlarged hook part, FIG. 11B is an enlarged side view illustrating the enlarged side surface of the hook part, and FIG. 11C is an enlarged perspective view illustrating the enlarged alignment part.

DESCRIPTION OF THE PREFERRED EMBODIMENTS

Embodiment

A cover structure and a medical device according to an embodiment of the present invention are described in reference to FIGS. 1 to 5A-5D. Configurations of the cover structure and the medical device according to the present embodiment are described referring to FIGS. 1 to 4. The medical device of the present embodiment is mainly described below, since the cover structure according to the present embodiment is inseparable from the medical device according to the present embodiment.

Figure 1:
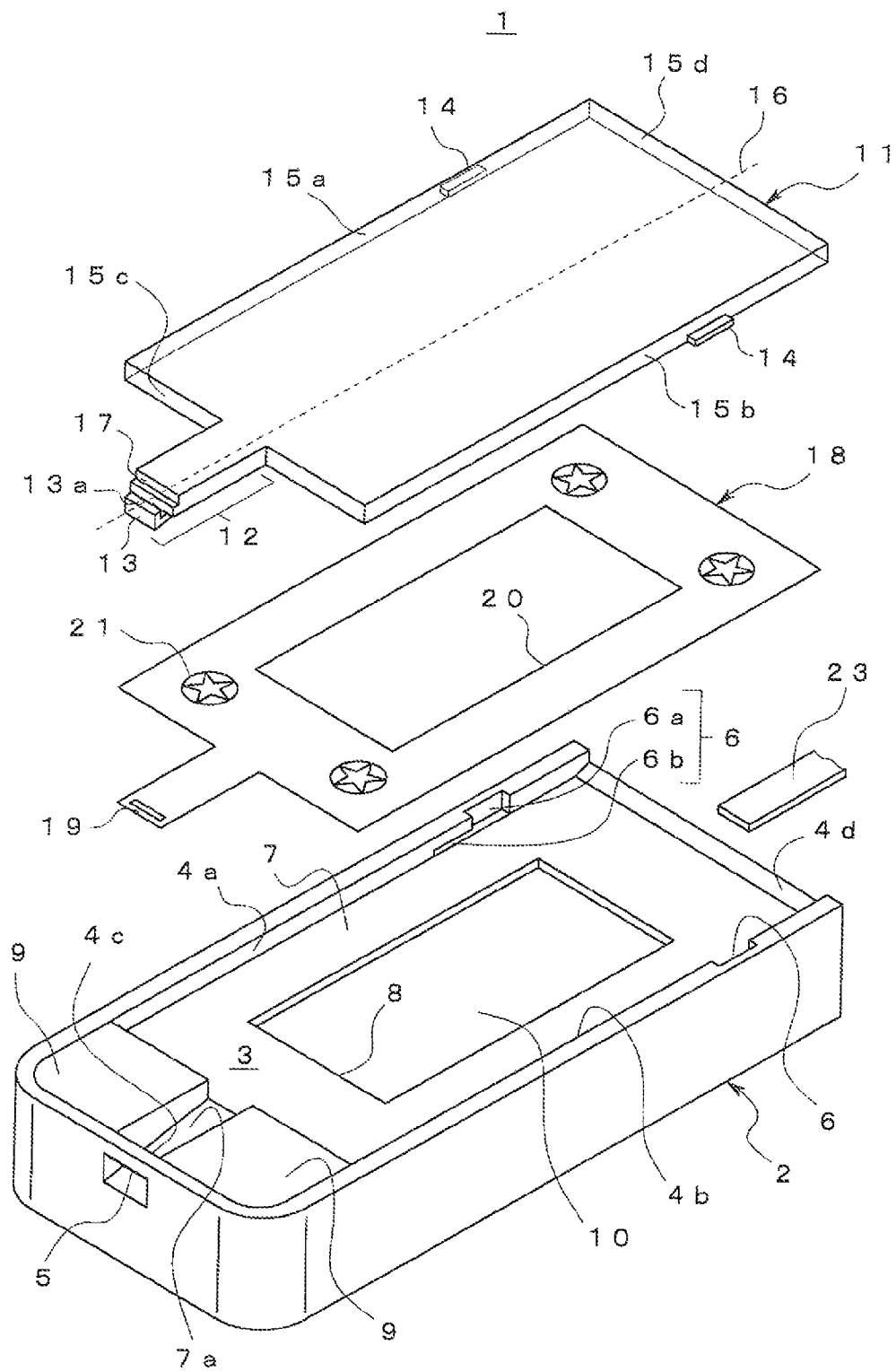
FIG. 1 is an exploded perspective view illustrating main components of a medical device according to an embodiment of the present invention.
Figure 2:
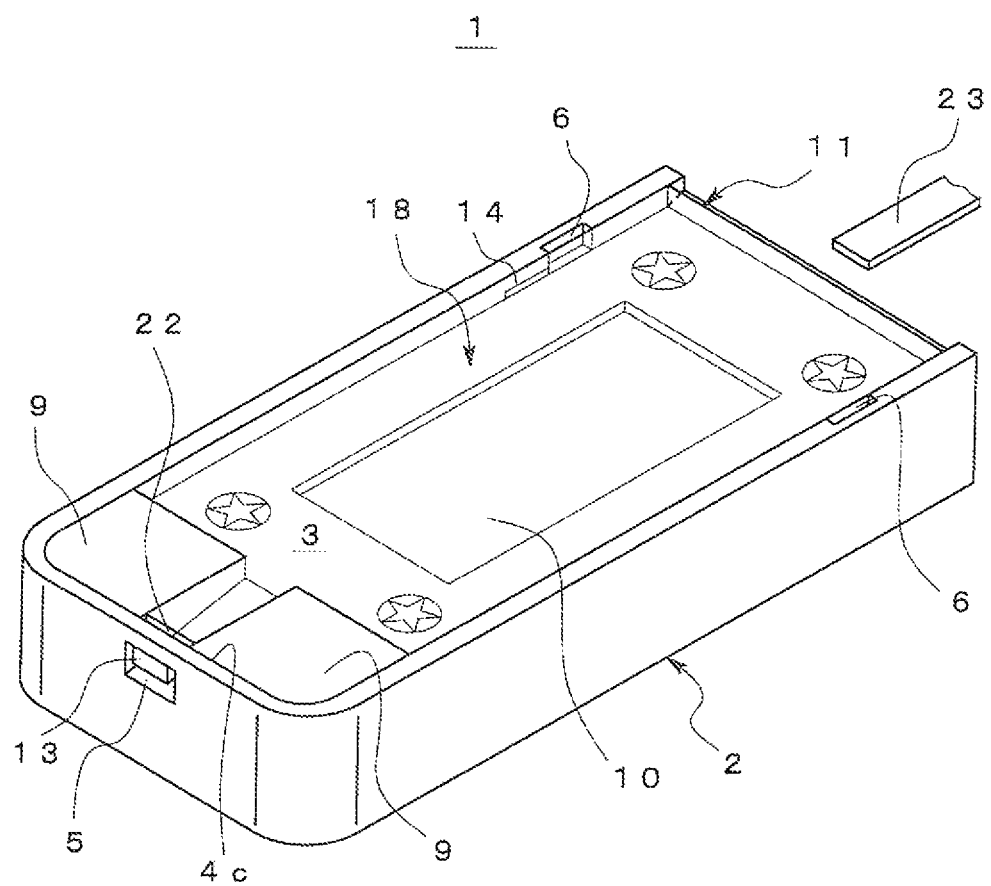
FIG. 2 is a perspective view illustrating an appearance of the medical device according to the embodiment of the present invention, illustrating the medical device as assembled using the components illustrated in FIG. 1.

FIG. 1 is an exploded perspective view illustrating main components of the medical device according to the embodiment of the present invention. FIG. 2 is a perspective view illustrating an appearance of the medical device according to the embodiment of the present invention, illustrating the medical device as assembled using the components illustrated in FIG. 1.

Figure 3A:
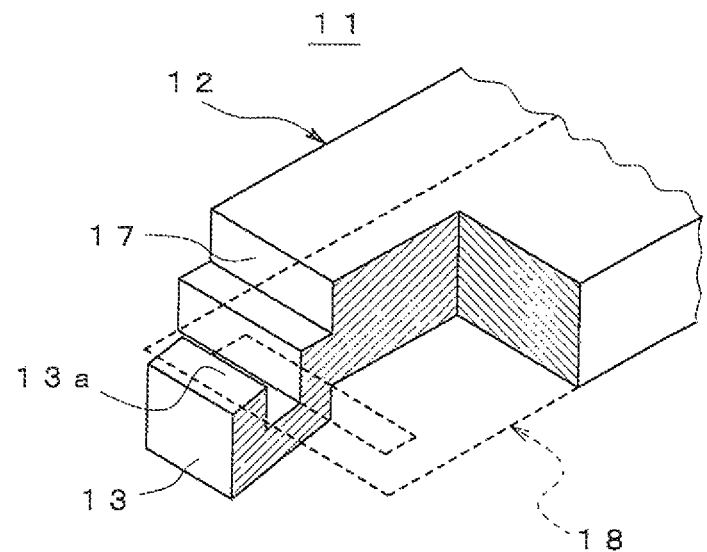
FIGS. 3A to 3C are diagrams illustrating part of a cover member and a sheet member.
Figure 3B:
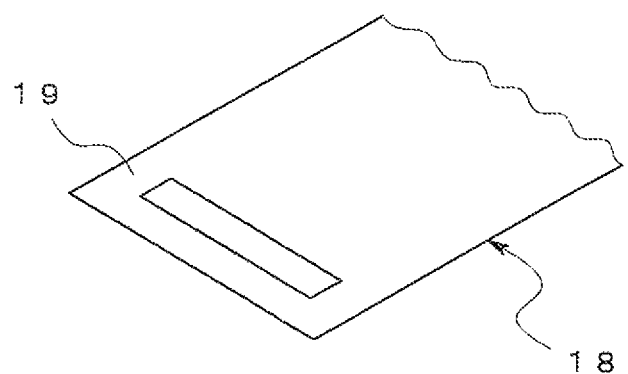
Figure 3C:
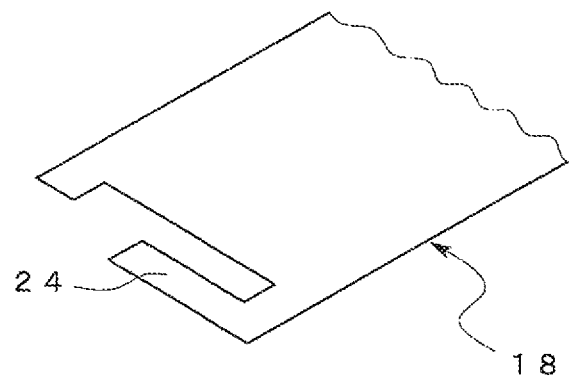
Figure 4:
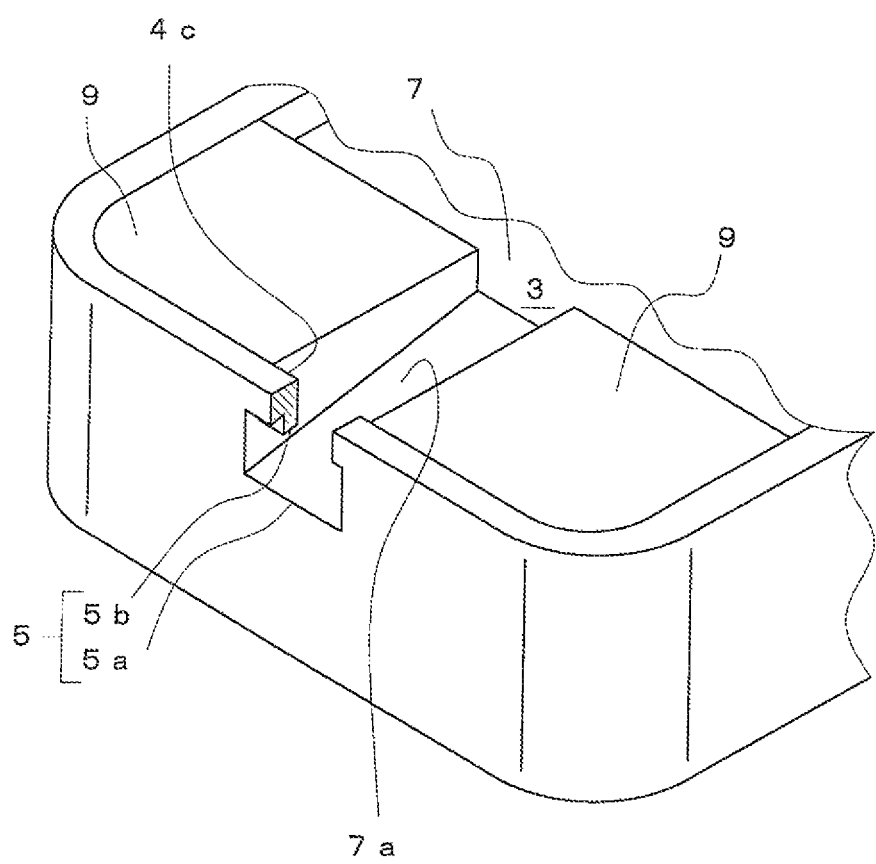
FIG. 4 is a perspective view illustrating an enlarged part of a casing illustrated in FIG. 1. A cross section of the casing illustrated in FIG. 4 is also partially illustrated, which is indicated by hatching.

FIGS. 3A to 3C are diagrams illustrating part of a cover member and a sheet member. Among these, FIG. 3A is an enlarged perspective view illustrating an enlarged part of the cover member illustrated in FIG. 1, and FIG. 3B is an enlarged perspective view illustrating an enlarged part of the sheet member illustrated in FIG. 1. FIG. 3C is an enlarged perspective view illustrating an enlarged part of another example of the sheet member. In FIG. 3A, a cross section of a part of the cover member is illustrated, which is indicated by hatching. FIG. 4 is a perspective view illustrating an enlarged part of a casing illustrated in FIG. 1. A cross section of the casing illustrated in FIG. 4 is also partially illustrated, which is indicated by hatching.

A medical device 1 illustrated in FIGS. 1 and 2 is a medical device that measures a condition of a living body, including, for example, a glucose meter, a sphygmomanometer, a lactate meter, a ketone body measuring device, a thermometer, a urine analyzer, and a lipid measuring device. The medical device 1 includes a casing 2, inside which, a measuring device (not illustrated in FIG. 1) according to the intended use is housed. The medical device 1 is configured in a hand-held size, and is assumed to be carried by a user such as a patient, a doctor, and a nurse.

The medical device 1 in the present embodiment is a portable glucose meter that measures the blood glucose level of a patient's blood. In the present embodiment, the patient's blood is provided by a strip-like sensor 23. The sensor 23 is inserted into a sensor insertion opening (not illustrated) provided at the casing 2. The sensor 23 contains a reagent inside, and the blood reacts with the reagent inside the sensor 23 beforehand. The measuring device inside the casing 2 has a function of measuring the blood glucose level from the blood that has reacted with the reagent by a colorimetric or electrochemical method. Measurement by the measuring device is started immediately after insertion of the sensor 23 into the sensor insertion opening. The measurement result is displayed on a display screen 10 provided at the casing 2.

As illustrated in FIGS. 1 and 2, the medical device 1 according to the present embodiment includes a cover member 11 and a sheet member 18 in addition to the above-described casing 2. Moreover, the cover structure according to the present embodiment also includes the casing 2, the cover member 11, and the sheet member 18. In the cover structure, the casing 2 serves as a base of the cover structure.

The sheet member 18 is interposed between the casing 2 and the cover member 11. In the present embodiment, the cover member 11 has optical transparency, so that the user can see the sheet member 18 through the attached cover member 11. In FIG. 2, an object that is seen through the optically transparent cover member 11 is indicated by a fine line.

As illustrated in FIG. 1, the cover member 11 covers a portion on one-direction side of the casing 2. The cover member 11 includes on its periphery a hook part 12 having a hook-like portion 13 and protrusions 14. The "portion on one-direction side" to be covered here means a portion that is observed when a observer observes the casing 2 from an arbitrary direction, that is, a portion on the observer's side of the casing 2.

Thus the "portion on one-direction side" does not include a portion that can not be observed without changing an observation direction, in which the cover member 11 is different from the conventional covers (Patent documents 1 and 2) which cover an upper surface and all side surfaces of a casing at a time. The "portion on one-direction side" may be the whole of a portion that is observed or may be only a part.

In the present embodiment, a portion that is observed when the casing 2 is observed from the above along a normal line of the display screen 10, that is, a portion on the display screen side of the casing 2 is the "portion on one-direction side" to be covered. More specifically, "the portion on one-direction side" is a bottom surface 7 of a recess 3 provided on the display screen side of the casing 2. Also in the present embodiment, the cover member 11 is in the form of a plate and includes two opposing side surfaces 15a and 15b. Each of the side surfaces 15a and 15b has a protrusion 14.

The hook part 12 is arranged on a virtual axis 16 being parallel to the two side surfaces 15a and 15b and passing between one of the protrusions 14 and the other protrusion 14. More specifically, as illustrated in FIGS. 1 and 3A-3C, the hook part 12 projects from a side surface 15c that is adjacent to the side surfaces 15a and 15b, being formed integrally with the plate-like portion. A hook-like portion 13 is provided at the tip of the projecting portion. In the present Description, "arranged (located) on a virtual axis" means a target object (or a target portion) overlaps the virtual axis when the cover member 11 is seen from either one of the principal surface sides.

As illustrated in FIGS. 1 and 3A, the hook part 12 in the present embodiment is shaped such that the tip 13a of the hook-like portion 13 faces the opposite side from the casing 2 side (upward in the figure) when the cover member 11 is arranged on the casing 2. This enables the user to disconnect the hook part 12 from a below-described latch part 5 (see FIG. 4) by pushing the hook part 12 (or a portion on the hook part 12 side) of the cover member 11 from outside as described below referring to FIGS. 5A to 5D.

As illustrated in FIGS. 1 and 4, the casing 2 includes the latch part 5 configured to engage with the hook part 12 and fitted portions 6 for the protrusions 14 to fit in. The casing 2 in the present embodiment includes a recess 3 in a portion to be covered by the cover member 11. The latch part 5 is provided in a position of a side wall of the recess 3 corresponding to the hook part 12, and the fitted portions 6 are provided in a position of the side wall of the recess 3 corresponding to the protrusions 14.

More specifically the position of the side wall of the recess 3 corresponding to the hook part 12 is on a side wall 4c of the recess 3 facing the hook part 12. The position of the side wall of the recess 3 corresponding to the protrusions 14 is on side walls 4a and 4b of the recess 3 facing the protrusions 14. The recess 3 is shaped to fit with the outer shape of the cover member 11, and the shape of the opening of the recess 3 conforms to the outer shape of the cover member 11. The recess 3 is provided such that the cover member 11 fits in the inside of the recess 3.

In the present embodiment, the display screen 10 is arranged at the bottom surface 7 of the recess 3, and thus the recess 3 includes an open part 8 at the bottom surface 7. The display screen 10 is exposed externally through the open part 8. The cover member 11 serves as a protective cover that protects the display screen 10 from outside.

As illustrated in FIG. 4, the latch part 5 in the present embodiment includes a hole 5a provided in a position of the side wall 4c corresponding to the hook part 12 and projections 5b provided inside the hole 5a. The hole 5a is provided so as to allow insertion of the hook-like portion 13 in a position corresponding to the hook part 12. The projections 5b are configured to engage with the hook-like portion 13 (see FIG. 3A).

More specifically, since the tip 13a of the hook-like portion 13 faces upward in the figure (see FIG. 3A), as illustrated in FIG. 4, the projections 5b are shaped so as to protrude downward in the figure (toward the bottom surface 7 of the recess 3) from an inner wall of the hole 5a. The projections 5b are also shaped to fit in the inner side of a hook (see FIGS. 5A to 5D).

With such a configuration, when the cover member 11 is slid (see FIGS. 1 and 3A) and the hook part 12 is pushed into the latch part 5, the hook-like portion 13 and the projections 5b come into contact, elastically deform each other in some cases, and then meshes with each other. The present embodiment allows easy engagement of the hook-like portion 13 with the projections 5b. This is described below, referring to FIGS. 5A to 5D. In the present embodiment, the hole 5a of the latch part 5 is a through hole that passes through the side wall 4c, but is not limited thereto. The hole 5a may be a blind hole (recess) in the side wall 4c.

As illustrated in FIG. 1, the fitted portions 6 in the present embodiment include longitudinal grooves 6a and transverse grooves 6b. The longitudinal grooves 6a and the transverse grooves 6b are provided in a position of each of the side walls 4a and 4b corresponding to the protrusions 14. The longitudinal grooves 6a are provided from the opening of the recess 3 along the depth of the recess 3. The transverse grooves 6b are provided along the bottom surface 7 of the recess 3 so as to intersect (more specifically, intersect at right angles) with the longitudinal grooves 6a.

Furthermore, the cross sectional shape of the longitudinal grooves 6a perpendicular to the depth of the recess 3 conforms to the cross sectional shape of the protrusions 14 in a planer direction of the cover member 11 (see FIG. 1). Moreover, the height of the transverse grooves 6b along the depth of the recess 3 conforms to the height of the protrusions 14 along the thickness of the cover member 11 (see FIG. 1).

Thus the protrusions 14 are fitted into the fitted portions 6 by aligning the protrusions 14 of the cover member 11 with the longitudinal grooves 6a of the recess 3, and then pushing the cover member 11 from above and sliding it. Releasing from this fit only requires that the cover member 11 is slid so that the protrusions 14 come to the longitudinal grooves 6a. This is described below, referring to FIGS. 5A to 5D. Instead of a groove, a slit or a through hole may be employed in the present embodiment.

As illustrated in FIGS. 1 and 4, an inclined plane 7a is provided in an area of the bottom surface 7 of the recess 3 on the hook part 12 side such that the recess 3 becomes deeper toward the side wall 4c in the present embodiment. This allows the hook part 12 (more specifically, the hook-like portion 13) to move to the bottom surface 7 side of the recess 3 when the hook part 12 (or a portion on the hook part 12 side) of the cover member 11 is pushed from outside. In the present embodiment, the connection between the hook part 12 and the latch part 5 (see FIG. 4) is released by movement of the hook part 12. In order not to obstruct the movement of the hook-like portion 13, the hole 5a of the latch part 5 is shaped such that its opening agrees with the inclined plane 7a.

In FIGS. 1, 2 and 4, 9 indicates an operation button of the medical device 1. A portion facing the cover member 11 of side surfaces of the operation buttons 9 constitutes a side wall of the recess 3 in the present embodiment. In order to facilitate attachment and detachment of the cover member 11, the side wall of the recess 3 is preferably shaped such that a portion opposing a position corresponding to the hook part 12 is lower than other portions in the present embodiment. This opposing portion is a portion where the virtual axis 16 passes (that is, a portion located on the virtual axis 16) when the cover member 11 is attached.

The side wall 4d opposing the side wall 4c is lower than the side walls 4a to 4c and the side wall configured by the operation buttons 9 in the present embodiment. More specifically, as illustrated in below-described FIG. 5A, the height hd of the side wall 4d is lower than the height ha of the side walls 4a and 4b, the height hc of the side wall 4c, and the heights ha to hd of the side wall by the operation buttons 9.

The "height of the side wall" in the present embodiment means a distance between a plane including a boundary between the target side wall and the bottom surface 7 and a plane being parallel to this plane and including the highest portion (the top side or the apex) of the target side wall. For example, the height hc of the side wall 4c is from the boundary between the inclined plane 7a and the side wall 4c to the upper surface of the side wall 4c (see FIG. 5A). When the side wall has a triangular (or trapezoidal) cross section like the side wall 4d, the height of the triangle (or trapezoid) is the height hd of the side wall.

As illustrated in FIGS. 1 and 3B, the sheet member 18 includes an alignment part 19 for aligning itself with the cover member 11. The alignment part 19 is configured to engage with a part of the cover member 11. More specifically, the alignment part 19 includes a ring-like portion. The ring-like portion is provided so as to allow insertion of the hook-like portion 13 in an inner side (open part) of its inner circumference, allowing engagement with the hook-like portion 13, as indicated by a broken line in FIG. 3A. Consequently, the sheet member 18 is aligned with the cover member 11. The sheet member 18 is interposed between the cover member 11 and the casing 2 in this state (see FIG. 2).

As illustrated in FIG. 3C, the sheet member 18 in the present embodiment may include an alignment part 24, instead of the alignment part 19. The alignment part 24 includes a U-shaped portion, by which it engages with the hook-like portion 13. The sheet member 18 is aligned with the cover member 11 also when the alignment part 24 illustrated in FIG. 3C is employed.

The sheet member 18 in the present embodiment also includes an open part 20 to expose the display screen 10. Furthermore, a pattern 21 is exhibited on an surface of the sheet member 18 on the cover member 11 side. There is no particular limitation with respect to the shape, the color, and the like of the pattern 21 in the present embodiment. Letters may be exhibited instead of or in addition to the pattern 21.

Figure 5A:
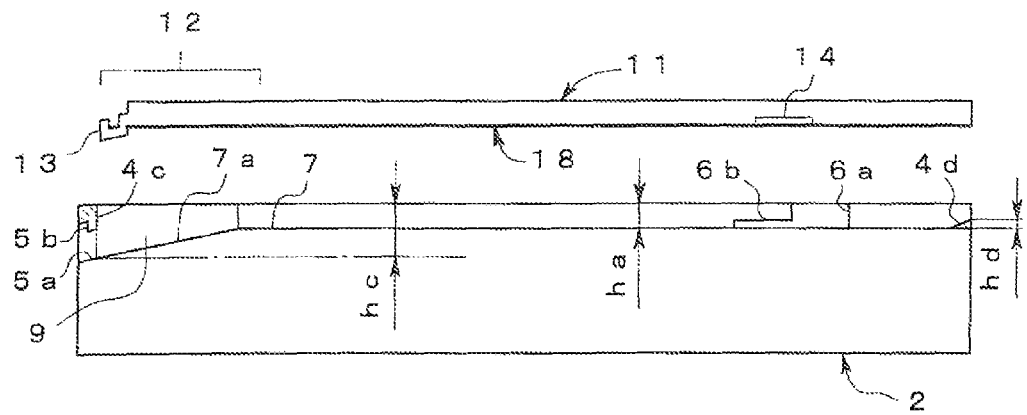
FIGS. 5A to 5D are diagrams illustrating attachment and detachment of the cover member and the sheet member illustrated in FIGS. 1 to 3A-3C.
Figure 5B:
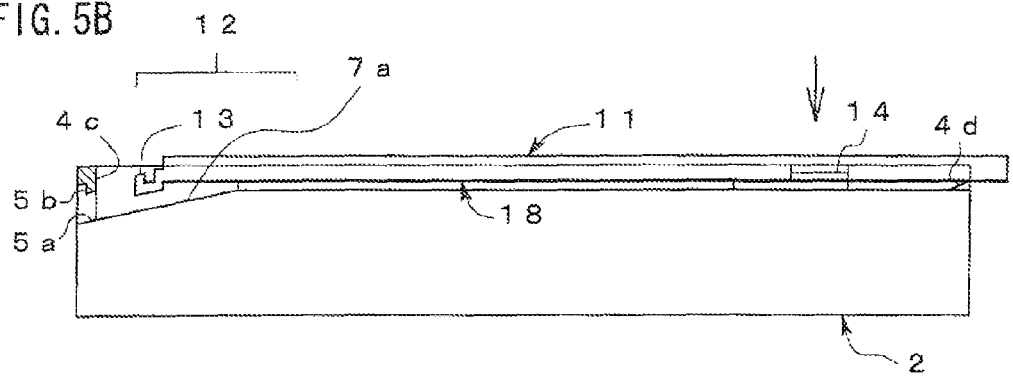
Figure 5C:
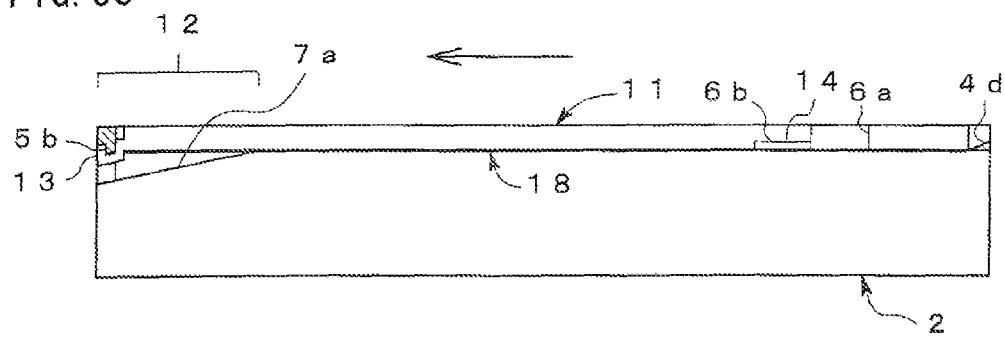
Figure 5D:
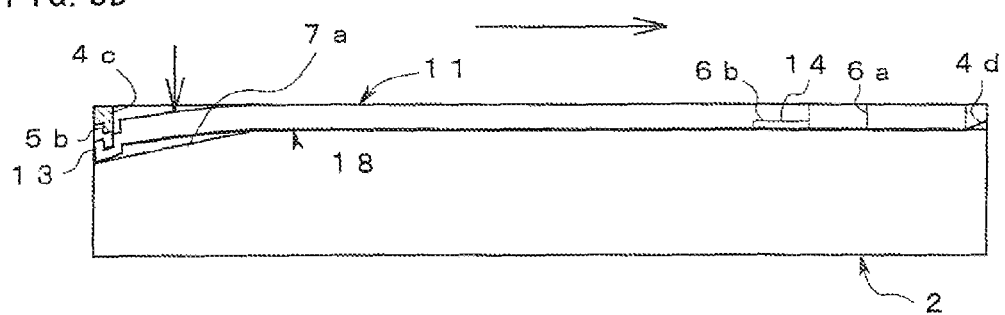

Described next referring to FIGS. 5A to 5D are attachment to and detachment from the casing 2 of the cover member 11 and the sheet member 18. FIGS. 5A to 5D are diagrams illustrating attachment and detachment of the cover member and the sheet member illustrated in FIGS. 1 to 3A-3C. FIGS. 5A to 5C illustrate a series of attachment steps and FIG. 5D illustrates a detachment step. FIGS. 5A to 5D illustrate a cross section of the cover member 11, the sheet member 18, and the side walls 4c and 4d of the recess 3 of the casing 2. Among these, the side walls 4c and 4d of the recess 3 are hatched.

When attaching the cover member 11, a user first inserts the hook-like portion 13 into the open part (see FIG. 3B) of the ring-like portion of the sheet member 18 and superpose the sheet member 18 on the cover member 11, as illustrated in FIG. 5A. The sheet member 18 is thus aligned with the cover member 11. The present embodiment does not require positioning of the sheet member 18 on the casing 2 beforehand, unlike the example in Patent document 3.

As illustrated in FIG. 5B, the user next positions the cover member 11 such that the protrusions 14 of the cover member 11 agree with the opening of the longitudinal grooves 6a. In this state, the user then pushes the cover member 11 until the protrusions 14 reach the transverse grooves 6b. At this time, although a portion of the cover member 11 in contact with the side wall 4d and the surrounding area may elastically deform, the cover member 11 does not break and is not difficult to attach, since the side wall 4d is lower than the other side walls. In other words, the side wall 4d has an appropriate height so as not to render attachment of the cover member 11 difficult.

As illustrated in FIG. 5C, the user subsequently slides the cover member 11 toward the side wall 4c, and fits the protrusions 14 into the fitted portions 6 (see FIG. 1). Then the hook part 12 is pushed into the latch part 5, and the hook-like portion 13 and the projections 5b elastically deforms due to contact. The hook-like portion 13 and the projections 5b then meshes with each other, so that engagement of the hook-like portion 13 with the projections 5b is completed. This results in the state illustrated in FIG. 2.

When detaching the cover member 11, the user can push the hook part 12 of the cover member 11 first, as illustrated in FIG. 5D. This causes the hook part 12 to elastically deform, so that the hook-like portion 13 moves to the bottom surface 7 (inclined plane 7a) of the recess 3, and meshing between the hook-like portion 13 and the projections 5b is released.

Subsequently, when the user slides the cover member 11 toward the side wall 4d, the fit between the protrusions 14 and the fitted portions 6 is released, and the cover member 11 becomes unlocked and thus detachable. When the cover member 11 is not reused, a mode in which the hook-like portion 13 moves toward the bottom surface 7 (inclined plane 7a) of the recess 3 due to the plastic deformation of the hook part 12 may be employed.

As described above, the present embodiment does not need to employ a structure in which side surfaces are covered as disclosed in Patent documents 1 and 2, or a structure to be screwed as disclosed in Patent document 3. Furthermore, the cover member 11 itself has a structure that is not voluminous. Thus obstruction of size reduction of the device is prevented, unlike the examples disclosed in Patent documents 1 to 3. Moreover, since the cover member 11 is transparent in the present embodiment, changing the sheet member 18 to one with a different design realizes easy alteration in the appearance. In doing so, the sheet member 18 only needs to be attached to the cover member 11, and alignment of the sheet member 18 is not as complicated as the example in Patent document 3.

Because of a feature in the attachment structure in the present embodiment, a mechanism to attach the cover member 11 and the sheet member 18 to the casing 2 do not take a lot of space. Thus a structure in which the operation buttons 9 are exposed outside is realized, without a hole in the cover member 11 for operating the operation buttons 9. Consequently, operability is not hindered by the cover member 11.

Furthermore, such configuration as in the present embodiment allows easy attachment and detachment of the cover member 11 without a tool as illustrated in FIGS. 5A to 5D. In particular, appropriate settings of the height hd of the side wall 4d, the position of the hook part 12, and the shape of the bottom surface 7 of the recess 3 allow detachment of the cover member 11 only by sliding the cover member 11 away from the latch part 5 along the virtual axis 16.

It should be noted, however, that the lower the height hd of the side wall 4d is, the easier attachment and detachment of the cover member 11 is, but in such a case, the cover member 11 is more likely to be detached without intention of the user. The side wall 4d prevents the cover member 11 from being detached unintentionally by coming into contact with something external. Therefore, the height hd of the side wall 4d needs to be determined in light of balance between prevention of unnecessary detachment of the cover member 11 and facilitated attachment and detachment of the cover member 11.

In the present embodiment, an inclined plane like the inclined plane 7a may be provided also at the boundary with the side wall 4d side of the bottom surface 7. In such a case, the inclined plane is provided such that the casing 2 becomes thinner toward the side wall 4d. Attachment and detachment of the cover member 11 is facilitated also in such a case. Further in such a case, it is preferable that the cover member 11 is also provided with an inclined plane to fit with the inclined plane on the side wall 4d side, in order to maintain the unity between the cover member 11 and the casing 2.

It should be noted that the user may possibly not have enough physical strength to elastically deform the cover member 11 with bare hands. In order to cope with such a case, as illustrated in FIG. 2, the present embodiment may adopt a mode in which a gap 22 is provided between a surface 17 (see FIG. 3A) on the front side of the hook-like portion 13 and the side wall 4c, when the cover member 11 is attached. In this mode, a stick-like member can be inserted into the gap 22, so that the user can easily push the cover member 11 without the physical strength.

There is no particular limitation with respect to the formation material of the cover member 11 in the present embodiment. Moreover, the cover member 11 does not have to have optical transparency. On the other hand, when the cover member 11 has optical transparency, there is no limitation with respect to the transmissivity, and it may be semitransparent, as necessary. Examples of the formation material of the cover member 11 include resin materials in view of the flexibility in the shape.

Moreover, there is no limitation with respect to the number of protrusions 14 of the cover member 11. For example, the cover member 11 may be provided with only one protrusion 14 on a side surface opposing the hook part 12 (e.g. the side surface 15*d* (see FIG. 1)). In this mode, the recess 3 may be provided with a through hole or a recess for the protrusion 14 to fit in on the side wall 4*d* as the fitted portion 6.

There is no limitation with respect to the design applied to the sheet member 18 in the present embodiment. Moreover, the cover structure according to the present embodiment is also applicable to devices other than the above-described medical device, such as portable phones, PDAs, and electronic dictionaries. There is no particular limitation with respect to the device to which the cover structure according to the present embodiment is applicable.

Moreover, the shape of the hook-like portion 13 of the cover member 11, the shape of the alignment part of the sheet member 18, and the shape of the latch part 5 of the casing 2 in the present embodiment are not limited to the example illustrated in FIGS. 1 to 5A-5D. Other examples are described here referring to FIGS. 6 to 11A-11C.

Figure 6:
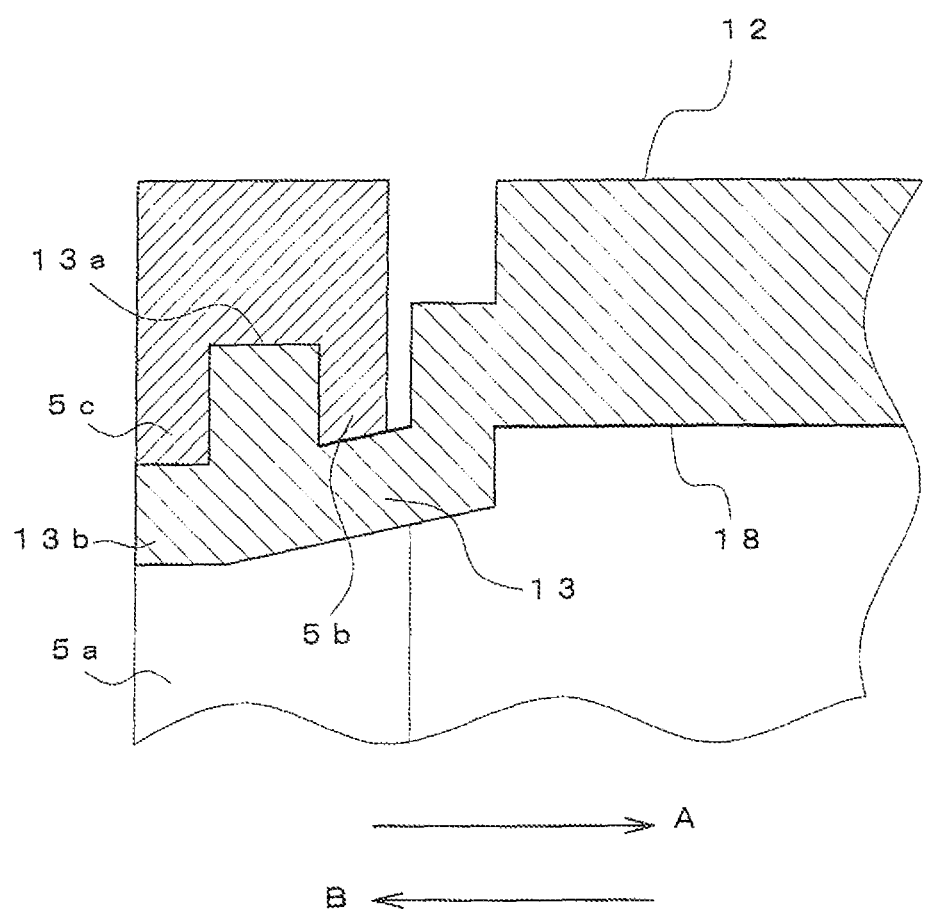
FIG. 6 is a cross-sectional view illustrating another example of the hook-like portion and the latch part in the present embodiment. The cross section illustrated in FIG. 6 is obtained along the cutting-plane line according to the cross sections illustrated in FIGS. 3A-3C and 4.

First referring to FIG. 6, an example of the latch part 5 having a different shape from the example in FIGS. 1 to 5A-5D is described. FIG. 6 is a cross-sectional view illustrating another example of the hook-like portion and the latch part in the present embodiment. The cross section illustrated in FIG. 6 is obtained along the cutting-plane line according to the cross sections illustrated in FIGS. 3A and 4. In the example illustrated in FIG. 6, projections 5*c* are provided inside the hole 5*a* in addition to the projections 5*b* to be paired therewith, unlike the example illustrated in FIGS. 1 to 5A-5D. The hook-like portion 13 is located between the projections 5*b* and the projections 5*c*, which are configured such that either one or both of them engage with the hook-like portion 13.

More specifically, in the example of FIG. 6, when the cover member 11 moves in the direction indicated by the arrow A (the direction toward the side wall 4*d* (see FIG. 1)), the projections 5*b* engage with the hook-like portion 13. In contrast, when the cover member 11 moves in the direction indicated by the arrow B (the direction toward the side wall 4*c* (see FIG. 1)), the projections 5*c* engage with the hook-like portion 13.

In this way, according to the example in FIG. 6, the area of the portion to engage with the hook-like portion 13 is increased, compared to the example in FIGS. 1 to 5A-5D. The example in FIG. 6 is useful for improvement in attachment strength of the cover member 11. Detachment can be done by pushing the hook part 12, in the same way as the example illustrated in FIG. 5D.

Also in the example in FIG. 6, the hook-like portion 13 includes a protrusion 13*b* at the end portion on the direction of insertion (direction of insertion in insertion into the hole 5*a*) side. The protrusion 13*b* is located near the base of a portion of the hook-like portion 13 to be inserted between the projections 5*b* and 5*c* (a portion including the tip 13*a*), and is in contact with the projections 5*c*. The protrusion 13*b* supports engagement between the hook-like portion 13 and the projections 5*c*.

Figure 7A:
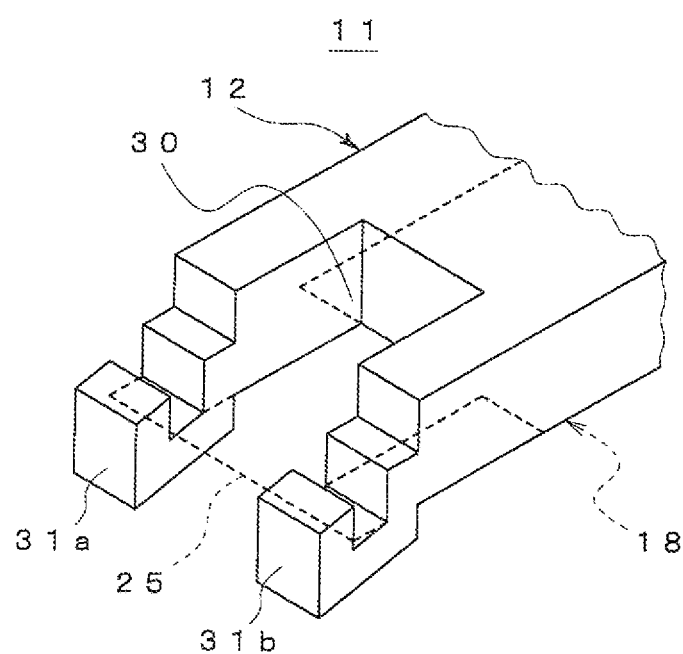
FIGS. 7A and 7B are diagrams illustrating another example of the hook part of the cover member and the alignment part of the sheet member in the present embodiment.
Figure 7B:
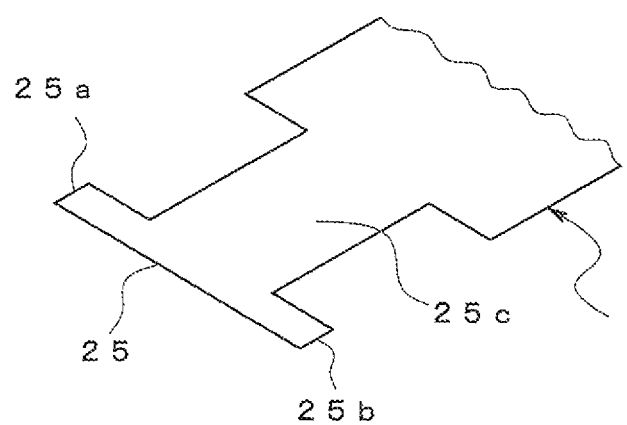
Figure 8A:
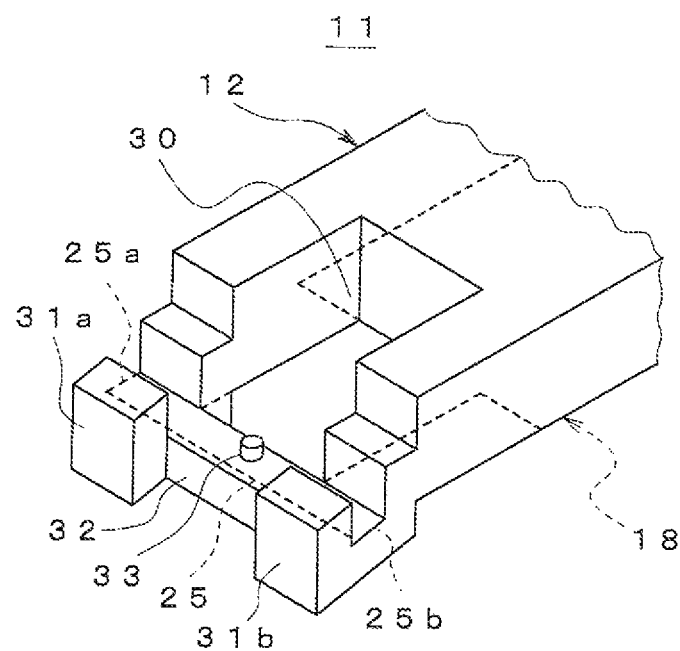
FIGS. 8A and 8B are diagrams illustrating another example of the hook part of the cover member and the alignment part of the sheet member in the present embodiment.
Figure 8B:
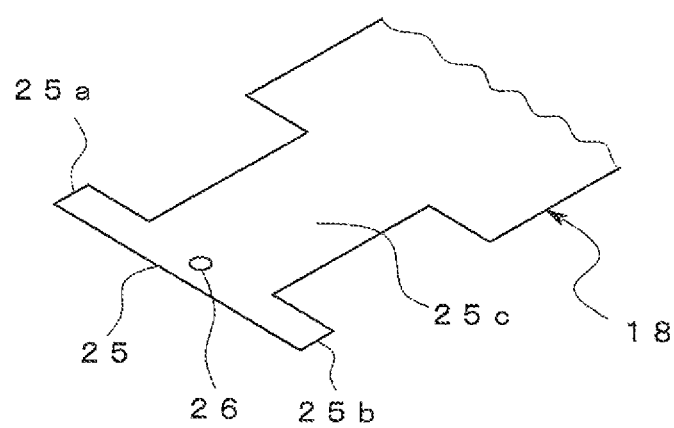
Figure 9A:
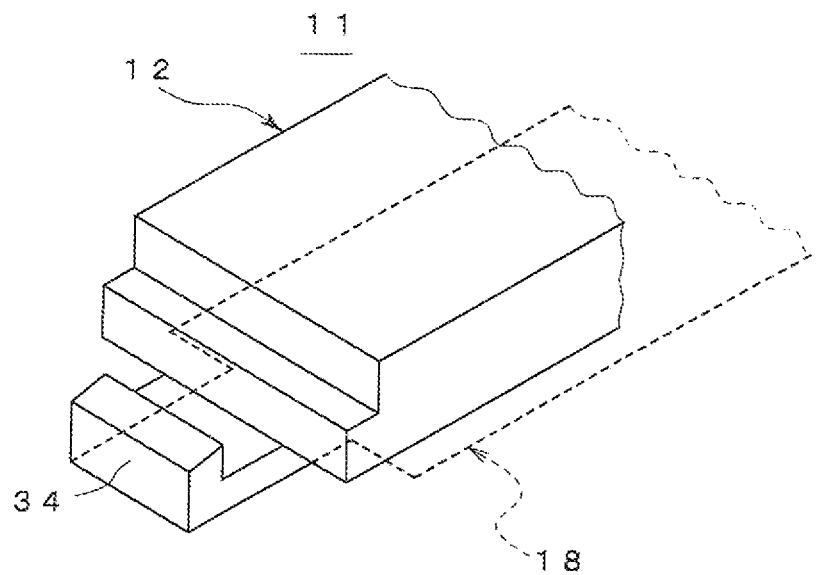
FIGS. 9A to 9C are diagrams illustrating another example of the hook part of the cover member and the alignment part of the sheet member in the present embodiment.
Figure 9B:
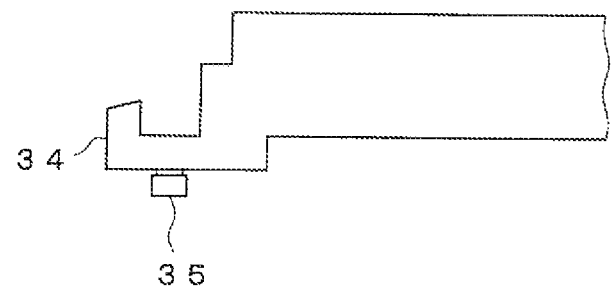
Figure 9C:
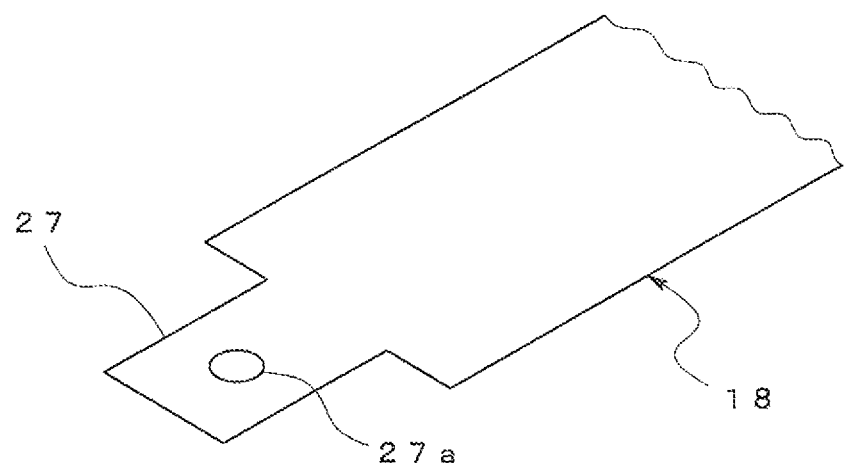
Figure 10A:
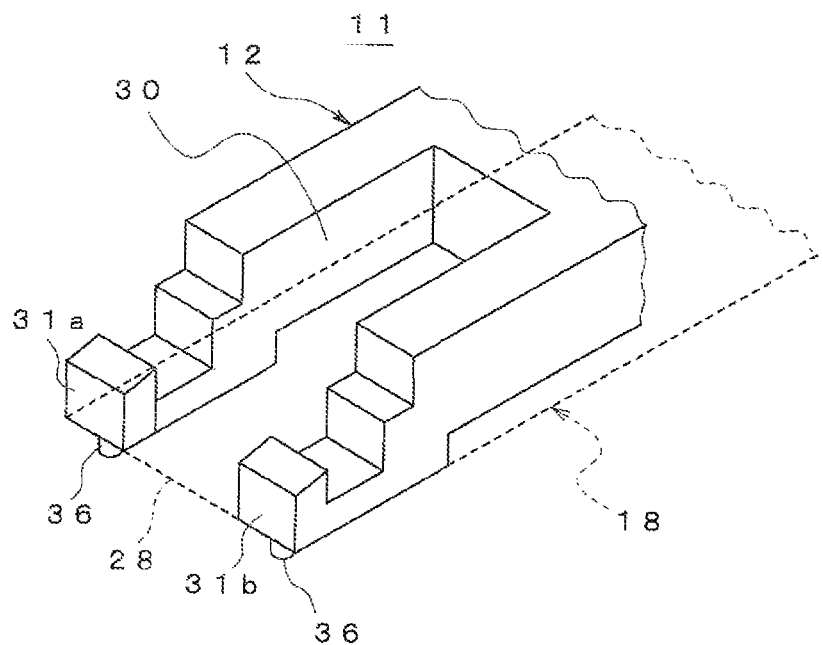
FIGS. 10A to 10C are diagrams illustrating another example of the hook part of the cover member and the alignment part of the sheet member in the present embodiment.
Figure 10B:
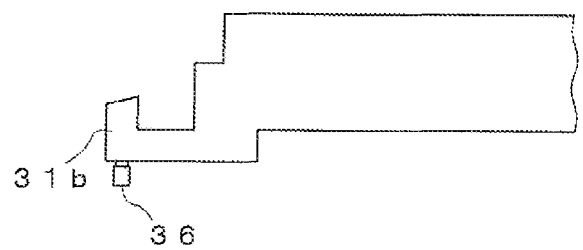
Figure 10C:
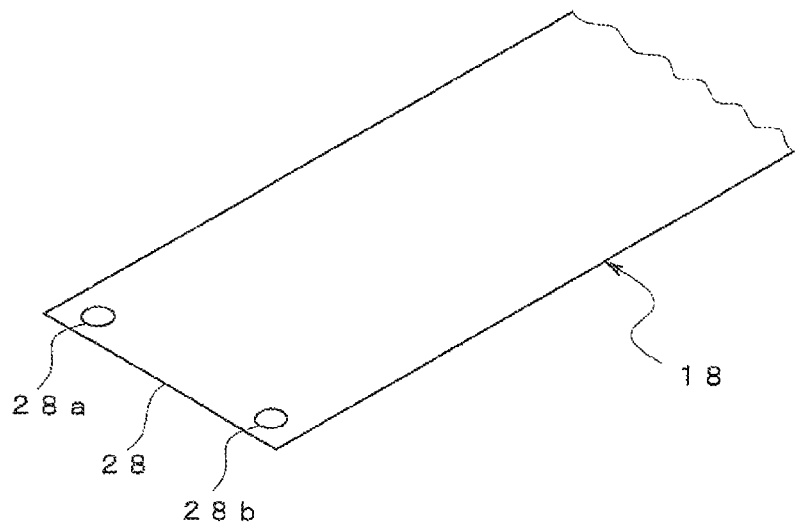
Figure 11A:
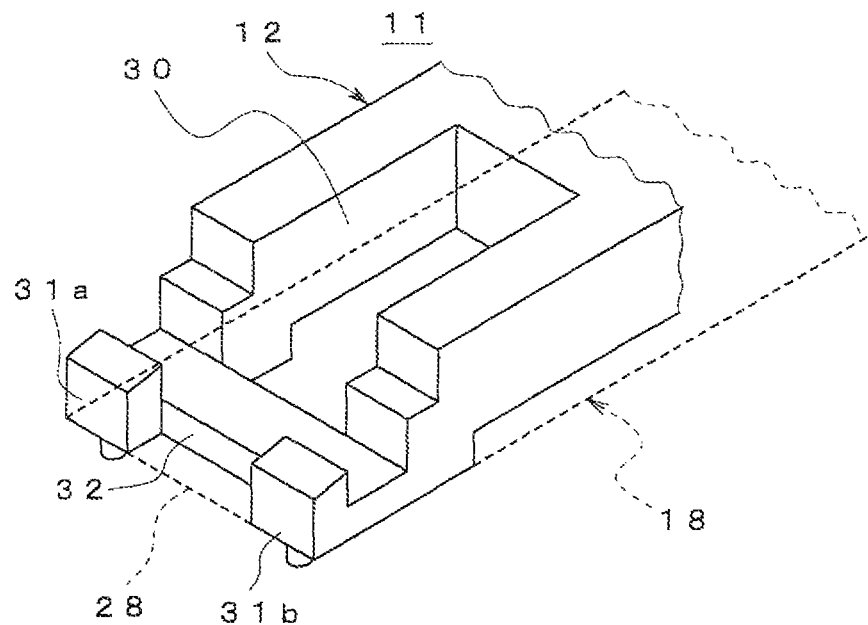
FIGS. 11A to 11C are diagrams illustrating another example of the hook part of the cover member and the alignment part of the sheet member in the present embodiment.
Figure 11B:
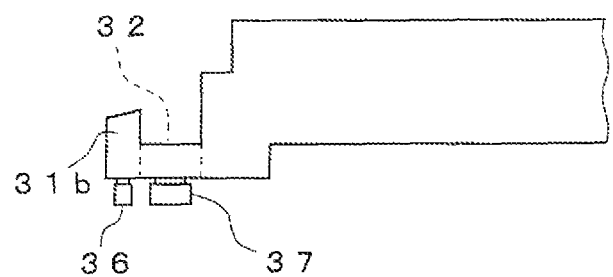
Figure 11C:
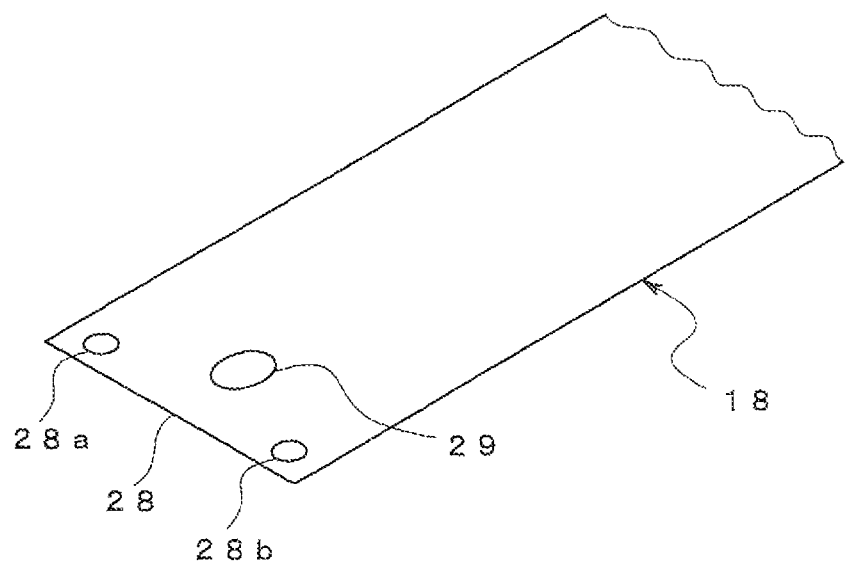

Next referring to FIGS. 7A-7B to 11A-11C, examples of the hook part 12 of the cover member 11 and the alignment part of the sheet member 18 different from the example in FIGS. 1 to 5A-5D are described. FIGS. 7A-7B to 11A-11C are diagrams illustrating other examples of the hook part of the cover member and the alignment part of the sheet member in the present embodiment. Among these, FIGS. 7A and 8A are enlarged perspective views illustrating the enlarged hook part, and FIGS. 7B and 8B are enlarged perspective views illustrating the enlarged alignment part. FIGS. 9A, 10A, and 11A are enlarged perspective views illustrating the enlarged hook part, FIGS. 9B, 10B, and 11B are enlarged side views illustrating an enlarged side of the hook part, and FIGS. 9C, 10C, and 11C are enlarged perspective views illustrating the enlarged alignment part. The sheet member 18 is indicated by broken lines in FIGS. 7A, 8A, 9A, 10A, and 11A.

As illustrated in FIG. 7A, the hook part 12 in the example in FIGS. 7A and 7B includes two hook-like portions, that is, a hook-like portion 31*a* and a hook-like portion 31*b*, unlike the example illustrated in FIG. 3A. The hook-like portion 31*a* and the hook-like portion 31*b* are provided at the tip of the hook part 12 so as to be parallel to each other. Moreover, a gap 30 is provided between the hook-like portion 31*a* and the hook-like portion 31*b*.

As illustrated in FIG. 7B, the sheet member 18 in the example in FIGS. 7A and 7B includes an alignment part 25 instead of the alignment part 19 illustrated in FIG. 1. The alignment part 25 includes a T-shaped portion. The T-shaped portion is provided with two tip portions 25*a* and 25*b* protruding in opposite directions. In the T-shaped portion, a portion 25*c* between the tip portion 25*a* and the tip portion 25*b* is shaped to fit with the gap 30.

Thus as illustrated in FIG. 7A, the sheet member 18 is aligned with the cover member 11, by leading the alignment part 25 from the gap 30 to the tip of the hook part 12, engaging the tip portion 25*a* with the hook-like portion 31*a*, and then engaging the tip portion 25*b* with the hook-like portion 31*b*. According to the example in FIGS. 7A and 7B, alignment of the sheet member 18 is facilitated.

As illustrated in FIG. 8A, the hook part 12 in the example in FIGS. 8A and 8B additionally includes a bridge 32 to bridge between the hook-like portions 31*a* and 31*b*. The bridge 32 is provided at a portion of the hook-like portions 31*a* and 31*b* furthest to the casing side (lower side in the figure, see FIG. 1), and has a protrusion 33 on the surface on the opposite side from the casing (upper side in the figure).

As illustrated in FIG. 8B, the sheet member 18 in the example in FIGS. 8A and 8B also includes an alignment part 25 in the same way as the sheet member 18 illustrated in FIG. 7B. It should be noted, however, that the alignment part 25 in the example in FIGS. 8A and 8B includes a through hole 26 that passes through the sheet member 18 along the thickness, in addition to the T-shaped portion. The through hole 26 is provided such that the protrusion 33 is inserted in the through hole 26 when the tip portions 25*a* and 25*b* of the T-shaped portion is respectively engaged with the hook-like portions 31*a* and 31*b*.

With such a configuration, alignment is further performed with the protrusion 33 and the through hole 26 in the example in FIGS. 8A and 8B. According to the example illustrated in FIGS. 8A and 8B, since the protrusion 33 and the through hole 26 engage, engagement strength between the hook part 12 and the alignment part 25 is increased, compared to the example in FIGS. 7A and 7B.

As illustrated in FIG. 9A, the hook part 12 in the example in FIGS. 9A to 9C includes a hook-like portion 34. The hook-like portion 34 has the same shape as the hook-like portion 13 illustrated in FIGS. 1 and 3A. It should be noted, however, that as illustrated in FIG. 9B, the hook-like portion 34 includes a columnar protrusion 35 on the casing side (lower side in the figure, see FIG. 1). The diameter of the protrusion 35 at the base portion is smaller than the diameter at other portions.

Moreover, as illustrated in FIG. 9C, the sheet member 18 in the example in FIGS. 9A to 9C includes an alignment part 27 instead of the alignment part 19 illustrated in FIG. 1. The alignment part 27 includes a through hole 27a that passes through the sheet member 18 along the thickness. The through hole 27a is provided in a position corresponding to the protrusion 35, and has a diameter to fit with the diameter of the base portion of the protrusion 35. The width of the alignment part 27 is smaller than the width of other portions, so as to fit with the width of the hook-like portion 34.

With such a configuration, alignment of the sheet member 18 in the example in FIGS. 9A to 9C with the cover member 11 is performed only by fitting the through hole 27a with the protrusion 35 from the lower side in the figure. According to the example illustrated in FIGS. 9A to 9C, alignment of the sheet member 18 is further facilitated.

As illustrated in FIG. 10A, the hook part 12 in the example in FIGS. 10A to 10C includes hook-like portions 31a and 31b in the same way as in the example in FIGS. 7A and 7B. It should be noted, however, that as illustrated in FIGS. 10A and 10B, the hook-like portions 31a and 31b in the example in FIGS. 10A to 10C both include columnar protrusions 36 on the surface on the casing side (lower side in the figure, see FIG. 1). The diameter of the protrusions 36 at the base portion is smaller than the diameter at other portions.

Moreover, as illustrated in FIG. 10C, the sheet member 18 in the example in FIGS. 10A to 10C includes an alignment part 28 instead of the alignment part 19 illustrated in FIG. 1. The alignment part 28 includes through holes 28a and 28b that pass through the sheet member 18 along the thickness. The through holes 28a and 28b are provided in a position respectively corresponding to the protrusions 36. Moreover, they have a diameter to fit with the diameter of the base portion of the protrusions 36.

Therefore, alignment of the sheet member 18 in the example in FIGS. 10A to 10C with the cover member 11 is performed only by fitting the through holes 28a and 28b respectively with the corresponding protrusions 36 from the lower side in the figure. Alignment in the example in FIGS. 10A to 10C is also completed only by fitting from the lower side in the figure, in the same way as in the example in FIGS. 9A and 9C. According to the example in FIGS. 10A and 10C as well, alignment of the sheet member 18 is further facilitated.

As illustrated in FIG. 11A, the hook part 12 in the example in FIGS. 11A to 11C includes the hook-like portions 31a and 31b and the bridge 32 in the same way as in the example in FIGS. 8A and 8B. It should be noted, however, that, as illustrated in FIG. 11B, the bridge 32 in the example in FIGS. 11A and 11C includes a protrusion 37 on the surface on the casing side (lower side in the figure, see FIG. 1). The protrusion 37 is shaped like a elliptic column, and its minor axis and its major axis at the base portion are smaller than its minor axis and its major axis at other portions. The hook-like portions 31a and 31b also in the example in FIGS. 11A to 11C both include columnar protrusions 36 on the surface on the casing side (lower side in the figure), in the same way as in the example in FIGS. 10A to 10C.

Moreover, as illustrated in FIG. 11C, the sheet member 18 in the example in FIGS. 11A to 11C also includes an alignment part 28 in the same way as the sheet member 18 illustrated in FIG. 10C. It should be noted, however, that the alignment part 28 in the example in FIGS. 11A to 11C also includes a through hole 29 that passes through the sheet member 18 along the thickness, in addition to the through holes 28a and 28b. The through hole 29 is provided in a position corresponding to the protrusion 37 provided for the bridge 32. The opening of the through hole 29 has a shape of an ellipse to fit with the cross sectional shape of the protrusion 37. Moreover, the through hole 29 has a minor axis and a major axis to fit with the minor axis and the major axis of the base portion of the protrusion 37.

Therefore, in the example in FIGS. 11A to 11C, the sheet member 18 is aligned with the cover member 11 by fitting the through holes 28a and 28b with the protrusions 36, and further, fitting the through hole 29 with the protrusion 37. According to the example illustrated in FIGS. 11A to 11C, engagement strength between the hook part 12 and the alignment part 28 is increased, compared to the example in FIGS. 10A to 10C. Alignment in the example in FIGS. 11A to 11C is also completed only by fitting from the lower side in the figure. According to the example in FIGS. 11A to 11C as well, alignment of the sheet member 18 is further facilitated.

In the examples in FIGS. 9A-9C to 11A-11C, there is no particular limitation with respect to the cross sectional shape of the protrusions and the shape of the opening of the through holes. They may have a rectangular or another polygonal shape. Moreover, instead of making the diameter of the protrusion smaller at the base portion, a groove may be provided at the base portion. This is because engagement between the inner circumference of the through holes and the protrusions can be increased even with such a mode.

As described above, the present invention is advantageous for medical devices, in particular, a small portable medical device, and further for portable phones, PDAs, electronic dictionaries, and the like. The cover structure and the medical device according to the present invention have industrial applicability.

While the invention has been described in detail, the foregoing description is in all aspects illustrative and not restrictive. It is understood that numerous other modifications and variations can be devised without departing from the scope of the invention.

What is claimed is:
1. A medical device that measures a condition of a living body, comprising:
  a casing including a latch part; and
  a cover member that includes a hook part to engage with the latch part and covers a portion on one-direction side of the casing, the hook part having a hook-like portion;
  one of the casing and the cover member including a protrusion, and the other including a fitted portion for the protrusion to fit in, wherein
  the casing includes a recess shaped to fit with an outer shape of the cover member at a portion to be covered by the cover member,
  the latch part is provided in a position of a side wall of the recess corresponding to the hook part,
  the fitted portion is provided in a position of the side wall corresponding to the protrusion,
  the hook part is shaped such that a tip of the hook-like portion faces an opposite side from a casing side when the cover member is arranged on the casing,
  the recess is configured to allow the hook part to move to a bottom surface side of the recess when the hook part of the cover member is pushed,
  the cover member is in a form of a plate and includes two opposing side surfaces, each of the two side surfaces having the protrusion, the hook part is arranged on a virtual axis being parallel to the two side surfaces and passing between the protrusions, and the side wall of the recess is shaped such that a portion located on the virtual axis when the cover member is attached and opposing a position corresponding to the hook part is lower than another portion.

2. The medical device according to claim 1, wherein the latch part includes a hole arranged in a position of the side wall of the recess corresponding to the hook part and a projection provided inside the hole, the hole is provided so as to allow insertion of the hook-like portion, and the projection is configured to engage with the hook-like portion.

3. The medical device according to claim 1, wherein the latch part includes a hole arranged in a position of the side wall of the recess corresponding to the hook part and a pair of projections provided inside the hole, the hole is provided so as to allow insertion of the hook-like portion, and the pair of projections are configured such that the hook-like portion is located between the pair of projections and at least one of the pair of projections engage with the hook-like portion.

4. The medical device according to claim 1, wherein the fitted portion includes a first groove and a second groove in a position of the side wall corresponding to the protrusion, the first groove is provided from an opening of the recess along the depth of the recess, and the second groove is provided so as to intersect with the first groove.

5. The medical device according to claim 1, further comprising:

a sheet member interposed between the casing and the cover member, the sheet member including an alignment part for aligning itself with the cover member.

6. A cover structure comprising:

a base including a latch part; and a cover member that includes a hook part to engage with the latch part and covers a portion on one-direction side of the base, the hook part having a hook-like portion, one of the base and the cover member including a protrusion, and the other including a fitted portion for the protrusion to fit in, wherein the base includes a recess shaped to fit with an outer shape of the cover member at a portion to be covered by the cover member, the latch part is provided in a position of a side wall of the recess corresponding to the hook part, the fitted portion is provided in a position of the side wall corresponding to the protrusion, the hook part is shaped such that a tip of the hook-like portion faces an opposite side from a base side when the cover member is arranged on the base, the recess is configured to allow the hook part to move to a bottom surface side of the recess when the hook part of the cover member is pushed, the cover member is in a form of a plate and includes two opposing side surfaces, each of the two side surfaces having the protrusion, the hook part is arranged on a virtual axis being parallel to the two side surfaces and passing between the protrusions, and the side wall of the recess is shaped such that a portion located on the virtual axis when the cover member is attached and opposing a position corresponding to the hook part is lower than another portion.

7. The cover structure according to claim 6, wherein the latch part includes a hole arranged in a position of the side wall of the recess corresponding to the hook part and a projection provided inside the hole, the hole is provided so as to allow insertion of the hook-like portion, and the projection is configured to engage with the hook-like portion.

8. The cover structure according to claim 6, wherein the latch part includes a hole arranged in a position of the side wall of the recess corresponding to the hook part and a pair of projections provided inside the hole, the hole is provided so as to allow insertion of the hook-like portion, and the pair of projections are configured such that the hook-like portion is located between the pair of projections and at least one of the projections engage with the hook-like portion.

9. The cover structure according to claim 6, wherein the fitted portion include a first groove and a second groove in a position of the side wall corresponding to the protrusion, the first groove is provided from an opening of the recess along the depth of the recess, and the second groove is provided so as to intersect with the first groove.

10. The cover structure according to claim 6, further comprising:

a sheet member interposed between the base and the cover member, the sheet member including an alignment part for aligning itself with the cover member.

* * * * *